(12) United States Patent
Paulus et al.

(10) Patent No.: US 10,605,749 B2
(45) Date of Patent: Mar. 31, 2020

(54) METHOD OF ANALYZING AN OBJECT IN TWO STAGES USING A TRANSMISSION SPECTRUM THEN A SCATTERING SPECTRUM

(71) Applicant: Commissariat A L'Energie Atomique et Aux Energies Alternatives, Paris (FR)

(72) Inventors: Caroline Paulus, Grenoble (FR); Joachim Tabary, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 357 days.

(21) Appl. No.: 15/322,542

(22) PCT Filed: Jun. 25, 2015

(86) PCT No.: PCT/FR2015/051713
§ 371 (c)(1),
(2) Date: Dec. 28, 2016

(87) PCT Pub. No.: WO2016/001535
PCT Pub. Date: Jan. 7, 2016

(65) Prior Publication Data
US 2017/0131224 A1    May 11, 2017

(30) Foreign Application Priority Data
Jun. 30, 2014 (FR) ..................... 14 56212

(51) Int. Cl.
*G01N 23/20* (2018.01)
*G01N 23/201* (2018.01)
*G01N 23/087* (2018.01)

(52) U.S. Cl.
CPC ..... *G01N 23/20083* (2013.01); *G01N 23/087* (2013.01); *G01N 23/201* (2013.01);
(Continued)

(58) Field of Classification Search
CPC ......... G01N 23/2076; G01N 23/20025; G01N 23/20091; G01N 2223/316
(Continued)

(56) References Cited

U.S. PATENT DOCUMENTS

| 7,092,485 B2 * | 8/2006 | Kravis ................ G01N 23/20 378/57 |
| 2006/0140340 A1 | 6/2006 | Kravis |
| 2016/0223706 A1 * | 8/2016 | Franco ................ G01V 5/0025 |

FOREIGN PATENT DOCUMENTS

| WO | WO2006/075296 A1 | 7/2006 |
| WO | WO2007/068933 A1 | 6/2007 |

OTHER PUBLICATIONS

International Search Report issued in PCT Application No. PCT/FR2015/051713 dated Sep. 25, 2015, 6 pages.

* cited by examiner

*Primary Examiner* — Courtney D Thomas
(74) *Attorney, Agent, or Firm* — Brinks Gilson & Lione (57) ABSTRACT

A method for analyzing an object, includes irradiating the object with incident photon radiation, acquiring a spectrum transmitted by the object using a spectrometric transmission detector, determining at least one first property of the object from the transmission spectrum, verifying that at least one doubt criterion relating to the first property of the object is met, and translating the fact that the object contains a material that is potentially dubious for the application under consideration. A second part, carried out only when the doubt criterion is met, includes acquiring an energy spectrum scattered by the object using a spectrometric scattering
(Continued)

detector at an angle of 1° to 15°, and determining a second property of the object from at least the scatter spectrum and comparing at least the second property of the object with properties of standard materials stored in a database to identify the objects composition material.

12 Claims, 8 Drawing Sheets

(52) U.S. Cl.
CPC ..... *G01N 2223/03* (2013.01); *G01N 2223/04* (2013.01); *G01N 2223/045* (2013.01); *G01N 2223/054* (2013.01); *G01N 2223/304* (2013.01); *G01N 2223/50* (2013.01)

(58) Field of Classification Search
USPC ...................................................... 378/70–89
See application file for complete search history.

METHOD OF ANALYZING AN OBJECT IN TWO STAGES USING A TRANSMISSION SPECTRUM THEN A SCATTERING SPECTRUM

RELATED APPLICATIONS

This application is a Section 371 nationalization of PCT application No. PCT/FR2015/051713, filed Jun. 25, 2015, the entire contents of which are incorporated by reference herein.

TECHNICAL FIELD

The present invention concerns a method of analyzing an object by diffractometry, and an associated detection system.

BACKGROUND

Diffractometry relates to the irradiation of a material or object using a source of electromagnetic radiation, of X or gamma type, followed by the analysis of radiation from elastic scattering at a small angle. The expression "radiation from elastic scattering at a small angle" designates the radiation coherently scattered by the material or object at an angle less than 15°, or less even than 10°, relative to the direction of the radiation that is incident on the material or object. As a matter of fact, beyond 10°, elastic scattering, or Rayleigh scattering, becomes progressively negligible. It is known to use diffractometry to detect certain crystalline substances such as most explosives or numerous other dangerous or illegal structures.

The invention thus finds an application in the field of security, more particularly in the field of the detection of explosive materials in an item of baggage.

It is also useful in the medical field, for example for locating a tumor in a breast. More particularly, a publication by UCL (Pani, S. et al. "Characterization of breast tissue using energy-dispersive X-ray diffraction computed tomography". *Applied Radiation and Isotopes* 68, No. 10 (2010): 1980-1987) has been able to show the possibility of differentiating (adipose tissues, fibrous tissues, benign tumors, fibroadenomas, carcinomas, etc.) objects of biological tissues from breast biopsies thanks to the scattering measurement of these tissues.

The analysis of the radiation scattered at a small angle (it is to be noted that that the term "diffracted" is generally used for a crystalline material, whereas the term "scattered" is generally used for an amorphous material, but these two terms here are used interchangeably, and likewise for the terms scattering and diffraction) by a material is a method of physico-chemical analysis which provides information on the structure of the material thereby enabling better characterization of materials.

It is known that the analysis of the spectrum of the radiation scattered at a small angle, or scattering spectrum, makes it possible to establish a signature for the material examined.

For crystalline materials for example, when the wavelength of the irradiating X-rays is of the same order of magnitude as the interplanar spacing (a few angstroms), the scattered rays generate constructive or destructive interferences according to their energy and their scattering angle. The conditions for which the interferences are constructive are determined by Bragg's law. For a crystalline material, this law links the interplanar spacing, the scattered radiation energy and the scattering angle, according to the following equation:

$$E_{hkl} = n \frac{hc}{2d_{hkl}\sin(\theta/2)}$$

with:
$d_{hkl}$: interplanar spacing between the crystallographic planes of the irradiated crystal;
{hkl}: Miller indices
θ: scattering angle, that is to say the angle formed between the scattered radiation analyzed and the beam that is incident on the irradiated crystal;
h: Planck's constant;
c: the speed of light;
n: the order of the interference.

It is possible to identify the Bragg peaks by the momentum transfer defined by the following equation:

$$x = \frac{\sin(\theta/2)}{\lambda} = \frac{n}{2d_{hkl}}$$

Figure 1:
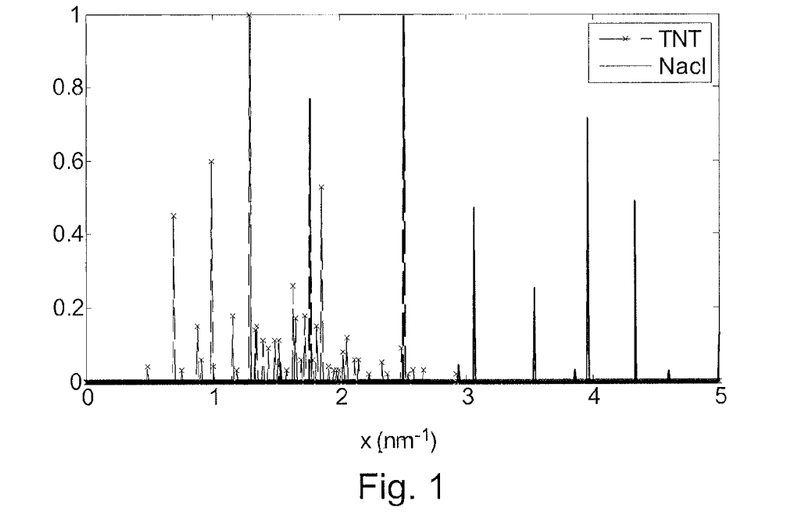
FIG. 1 is a graph representing the Bragg peaks of TNT (trinitrotoluene) and of salt (NaCl), which peaks illustrate the normalized intensity (y-axis), that is to say the relative number of photons detected during an acquisition operation, according to the momentum transfer x (x-axis) in $nm^{-1}$ of the detected photons.

The interest in expressing the scattering profiles (measured intensity) according to x is due to the fact that an intensity peak may be measured for different pairs (λ, θ) but for a single value of x (n fixed). By way of examples, appended FIG. 1 shows the Bragg peaks of two crystals, TNT (trinitrotoluene) and salt (NaCl).

In the case of non-crystalline materials, the spectrum for scattering at a small angle is also representative of the material examined.

Figure 2:
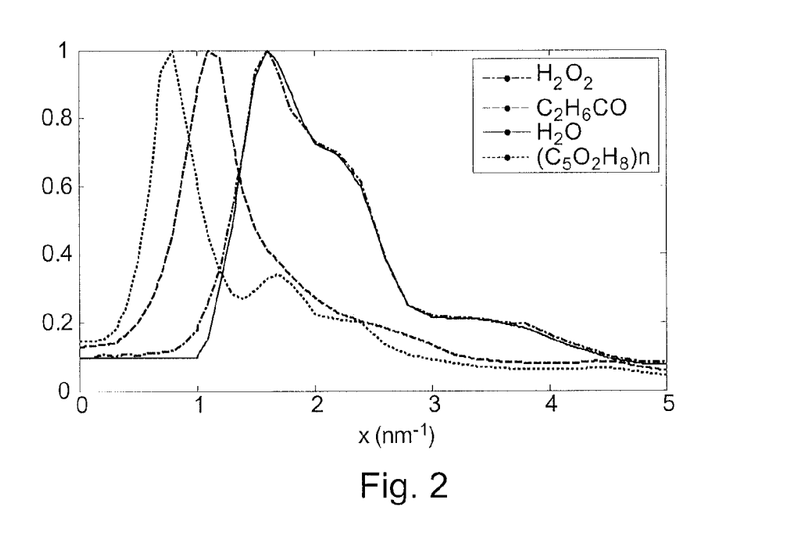
FIG. 2 is a graph representing the normalized molecular interference function of water ($H_2O$), the normalized molecular interference function of oxygenated water ($H_2O_2$), the normalized molecular interference function of acetone ($C_2H_6CO$), and the normalized molecular interference function of Plexiglas® (($C_5O_2H_8$)n), with, along the y-axis the number of photons detected and, along the x-axis, the momentum transfer x in $nm^{-1}$.

In the manner of the interferences determined by Bragg's law for a crystalline material, interference phenomena may also occur between the atoms and/or molecules of an amorphous material such as a liquid, this time involving a known distribution of distances (molecular interference function, denoted MIF). As a matter of fact, many amorphous materials have regular arrangements over nanometric distances (the expression short-range order used). This type of order is determined by strong chemical bonds for the covalent and ionic bonds. This short-range order causes intramolecular and intermolecular interferences. Appended FIG. 2 illustrates examples of molecular interference functions, i.e. the normalized MIF for water ($H_2O$), the normalized MIF for oxygenated water ($H_2O_2$), the normalized MIF for acetone ($C_2H_6CO$), and the normalized MIF of a material known under the tradename Plexiglas® (($C_5O_2H_8$)n).

The most common diffractometers are referred to as ADXRD (acronym for "Angular Dispersive X-ray Diffraction"). The energy is fixed by the use of monochrome radiation and the number of photons diffracted is measured according to the angle. Although these devices are very accurate, they require the use of a powerful monochrome source and cannot be used for imaging on account of their bulk.

Developed more recently, the EDXRD technique (EDXRD being the acronym for "Energy Dispersive X-Ray Diffraction") enables these difficulties to be alleviated. This time they consist in working at a fixed angle and using a set of collimators to illuminate the object with a polychromatic beam to measure the diffracted photons with an energy resolved spectrometric detector. The diffraction peaks then appear at certain energies in the measured spectrum.

The EDXRD technique, and more generally any technique of analysis by spectrometry, requires the employment of a spectrometric detector that is sufficiently energy resolving to enable the separation and the identification of the different characteristic peaks of the material constituting the object to analyze. The known detectors having the best energy resolution are of the Germanium type. However, this type of detector must be cooled to very low temperatures, by complex and/or costly methods (thermoelectric cooling or cooling by a tank of liquid nitrogen). Also, the analysis devices employing such a detector are very bulky.

The recent emergence of spectrometric detectors capable of being used at ambient temperature, such as detector types implementing CdTe, CdZnTe, or scintillator materials, provides an attractive alternative to the Germanium detectors. To be precise, these detectors are compact, not cooled and less costly. However, their performance in terms of energy resolution is still less than that obtained with the Germanium detectors, even though quite good.

To know whether a given crystalline or amorphous substance is contained in an object, it is thus known to:
- irradiate the object using an incident beam, emitted by a source of ionizing radiation, preferably collimated by a primary collimator,
- detect the diffracted radiation using a detection device comprising
  - a detector, here termed spectrometric detector, configured to establish an energy spectrum of the radiation scattered at a given scattering angle, that is to say a detector comprising
  - a detector material capable of interacting with radiation scattered by the object and which, on the side facing the object, presents what is referred to as a detection plane,
  - spectrometry measurement means, configured to measure an energy released by each interaction of a photon with the detector material and to establish at least one energy spectrum.
    - a collimator, referred to as detection collimator, associated with the detector, the detector and the detection collimator being arranged so as to have a detection axis D forming a scattering angle $\theta$ with the central axis Z of the incident beam,
  - analyzing the measured spectrum or spectra by comparison with the energy spectrum of the substance searched for.

In general terms, an energy spectrum illustrates the energy distribution of radiation in the form of a histogram representing the number of photon interactions in the object (along the y-axis) according to the released energy (along the x-axis). Often, the energy axis is discretized into channels of width 2 $\delta E$, a channel $C_i$, centered on the energy $E_i$ corresponding to the energies comprised between $E_i-\delta E$ and $E_i+\delta E$.

It is known that the identification of a material by the production then analysis of a scattering spectrum may be painstaking when it is wished to characterize objects of high volume. More particularly, this method is all the more accurate the smaller the volume of the object observed.

Furthermore, from WO 2006/075296 there is known a device and a method for identifying materials comprising a polychromatic source of X-rays, a detector configured for detecting radiation that is scattered (or diffracted) and radiation that is transmitted by the analyzed object, and a computing unit for:
- reconstructing an image of the object by tomography from the transmitted radiation, and comparing that transmission image with reference images to determine whether there is a suspicious region in the analyzed object,
- determining a first differential effective coherent scattering cross-section corresponding to a first momentum transfer of the detected scattered radiation for a suspicious region, and comparing this first differential effective cross-section with a first value corresponding to materials searched for,
- determining a second differential effective coherent scattering cross-section corresponding to a second momentum transfer of the detected scattered radiation for the suspicious region, and comparing this second differential effective cross-section with a second value corresponding to the materials searched for,
- determining a total effective cross-section for the suspicious region by summing the first and second differential effective cross-sections, and comparing that total effective cross-section with a third value corresponding to the materials searched for.

The length of execution of the method of WO 2006/075296 makes it incompatible with certain applications such as the search for explosive or dangerous products in baggage.

BRIEF SUMMARY

The invention is directed to alleviating these drawbacks, by providing in particular a method of analyzing an object that is faster and more effective.

For this, the invention provides a method for analyzing an object characterized in that it takes place in two parts, i.e. a first part comprising:
- irradiating the object with incident photon radiation,
- acquiring a spectrum of energy transmitted by the object, referred to as measured transmission spectrum, using a spectrometric detector placed for transmission,
- determining at least a first characteristic of the object based on the measured transmission spectrum,
- verifying the meeting of at least one criterion, referred to as suspicion criterion, concerning the first characteristic of the object and expressing the fact that the object contains a potentially suspicious material having regard to the application considered. Thus for example, in the case of an application relating to the field of security such as the search for explosives in baggage, the suspicion criterion expresses the fact that the object contains a potentially dangerous material, that is to say a material of which the first characteristic is similar to that of a an explosive material. In the case of a medical application such as the search for a tumor in a breast, the suspicion criterion expresses the fact that the object contains a potentially malignant material, that is to say a material of which the first characteristic is close to that of a cancerous tissue. A simple embodiment of the invention thus consists in using a suspicion criterion comprising at least one predefined range of values containing values of the first characteristic corresponding to materials searched for having regard to the application considered, that is to say a range of values for the first characteristic within which it is considered that the object is potentially suspicious having regard to the application considered, and outside of which the object is considered as not being suspicious. The verification of the suspicion criterion then comprises a step of comparing the first characteristic as determined previously for the object with the predefined range of values.

The method according to the invention comprises a second part which is carried out solely when the suspicion criterion is met.

Thus, when the suspicion criterion is not met, the analyzing method for the object is made to terminate at the end of the first part: the object in course of analysis is considered as inoffensive, is moved and possibly replaced (in the object receiving zone of the detection system) by a new object to analyze.

On the contrary, when the suspicion criterion is met, the second part is carried out, which second part comprises:

acquiring an energy spectrum, referred to as measured scattering spectrum, scattered by the object at a scattering angle θ comprised between 1° and 15° using a spectrometric detector placed for scattering, determining a second characteristic of the object from either the measured scattering spectrum, or the measured scattering spectrum and the measured transmission spectrum, comparing with characteristics of calibration materials stored in a database, or from the second characteristic of the object, or not only from the second characteristic of the object but also from the first characteristic of the object, for the purposes of identifying a material constituting the object.

In summary, the definition of the method provided above covers four cases:

a first case in which
the second feature (for example a scattering signature) is obtained only from the measured scattering spectrum, the transmission spectrum then only serving to eliminate the non-suspicious objects (in the first part of the method),
the second characteristic is used alone for identifying the material, it then being possible to qualify the second characteristic as a "determinant signature" of the material in the sense that by itself it makes it possible to identify the material reliably and rapidly, for example such as a scattering signature (Bragg Peaks, Molecular Interference Function), a second case in which
the second characteristic (for example scattering signature) is obtained from the measured scattering spectrum and from the measured transmission spectrum, the measured transmission spectrum then serving twice, a first time in the first part of the method to eliminate the non-suspicious objects and a second time in the second part of the method for determining the second characteristic for example to improve the accuracy with which that second characteristic is determined,
the second characteristic is used alone to identify the material, the second characteristic then being a determinant signature as defined supra, a third case in which
the second feature (for example momentum transfers) is obtained only from the measured scattering spectrum, the transmission spectrum then only serving to eliminate the non-suspicious objects (in the first part of the method),
both the second characteristic (for example momentum transfers) and the first characteristic (for example effective atomic number) are used to identify the material.

a second case in which
the second characteristic (for example the scattering signature itself, or the position of certain peaks of that scattering spectrum and possibly their relative intensity) is obtained from the measured scattering spectrum and from the measured transmission spectrum, the measured transmission spectrum then serving twice, a first time in the first part of the method to eliminate the non-suspicious objects and a second time in the second part of the method for determining the second characteristic for example to improve the accuracy with which that second characteristic is determined,
both the second characteristic (for example the scattering spectrum) and the first characteristic (for example a coefficient of attenuation, the thickness of a material constituting the object) are used to identify the material.

It is to be noted that it is possible to use one and the same spectrometric detector both for acquiring the transmission spectrum in the first part of the method, and for acquiring the scattering spectrum in the second part of the method. In this case, the detector should be moved in the course of the method, between the two positions of acquisition (position for transmission, on the axis of the incident radiation/position for scattering, offset by an angle θ from that axis).

As a variant, a detection system is used that is provided with two spectrometric detectors which are not provided to be moved, i.e. a spectrometric detector placed for transmission, and a spectrometric detector placed for scattering.

Advantageously and according to the invention, the first characteristic may correspond to a geometric shape of the object or to one of its dimensions, for example such as its thickness along the axis of incident radiation. The fact that the detector placed for transmission according to the invention is a spectrometric detector makes possible the estimation, as first characteristic of the object, in addition to those characteristics cited above, of a coefficient of attenuation for one or more predetermined energies, or for a given range of energies, or for instance of the effective atomic number $Z_{\mathit{eff}}$ of a material constituting the object. It may also be an indication as to the nature of a material constituting the object, for example such as:

a family of materials to which the material constituting the object belongs, the second part of the method then making it possible to specify within that family what is the exact nature of the material and thus refine the hypothesis provided by the first part, a hypothesis as to the actual nature of the material, the second part of the method then making it possible to confirm the hypothesis provided by the first step as to the nature of the material, these indications being obtained from the analysis of the transmission spectrum.

The effective atomic number $Z_{\mathit{eff}}$ is one of the parameters which may characterize a material. It is to be recalled that the atomic number of an element is defined as the number of protons present in the nucleus of an atom of that element. On the other hand, when a chemical compound is considered, the concept of effective atomic number must be used. This is defined as the atomic number of an element that would lead to the same transmission spectrum in a given energy band. In general, the effective atomic number of a chemical compound is obtained by means of a combination of the atomic numbers of the simple bodies constituting the compound, each atomic number being attributed a weighting coefficient depending on the fraction in terms of mass or atoms of the element in the compound. Thus, in practice, the effective atomic number $Z_{\mathit{eff}}$ of a compound of N single elements, verifies $$Z_{\textit{eff}} = \left( \sum_{i=1}^{N} \eta_i (Z_{\textit{eff}}^i)^p \right)^{1/p}$$

in which $Z_{\textit{eff}}$ is the atomic number of the element $i=1, \ldots, N$ and P is a constant linked to the photoelectric effect (p=4.62).

An advantage of determining the first characteristic from a measured transmission spectrum is that such a spectrum requires a relatively short acquisition and processing time compared to the acquisition of a scattering spectrum and also compared to the tomographic reconstruction carried out in WO 2006/075296, such that the first part of the method according to the invention, which does not enable the material to be identified precisely, but enables a high number of inoffensive objects to be eliminated, is fast. The second part of the method, which enables a better discrimination of the material but which is longer on account of the acquisition of a scattering spectrum, is only carried out on suspicious objects. A considerable time saving is thus achieved.

The second characteristic of the object, determined from at least one measured scattering spectrum, is for example a function called scattering signature, which represents scattering peaks (Bragg peaks for a crystalline material or molecular interference function for an amorphous material). As a variant, it may be a physical quantity extracted from such a scattering signature (interplanar spacing for a crystalline material for example). The second characteristic of the object may also be a momentum transfer.

As defined earlier, this second characteristic is determined from at least one measured scattering spectrum. In a preferred embodiment, it is determined from not only the scattering spectrum measured at the time of the second part of the method but also from the transmission spectrum measured at the time of the first part of the method.

The combined use of a scattering spectrum and of a transmission spectrum to reconstitute a scattering signature of a material is described in more detail below in the context of an example embodiment of the invention. This combination makes it possible to improve the identification of the material constituting the object.

In a preferred version, the spectrometric detector placed for scattering is configured so as to present a detection axis forming, with a central axis of the incident radiation, a scattering angle θ comprised between 1° and 10° and preferably between 1° and 5°.

In a preferred embodiment, the method of analysis according to the invention comprises a first prior step of calibrating a response matrix of the spectrometric detector placed for scattering (which calibrating step may be omitted in particular if the response of the detector is judged to be satisfactory, that is to say if the energy resolution of the detector used is particularly good), a second prior step of calibrating a response matrix of the detector placed for transmission when this is a spectrometric detector (which calibrating step may be omitted in particular if the response of the detector is judged to be satisfactory, that is to say if the energy resolution of the detector used is particularly good), and a third step of calibrating an angular response matrix of the detection system, it being possible for these first, second and third prior calibrating steps to be carried out in one order or in another, before any irradiation of an object to analyze, that is to say "off-line".

The invention covers a detection system provided to implement the method according to the invention, and in particular a detection system for the analysis of an object comprising:
- a source of photon radiation;
- a receiving zone for an object to analyze;
- detection means, downstream of the object receiving zone, for acquiring an energy spectrum, referred to as measured transmission spectrum, transmitted by the object and for acquiring an energy spectrum, referred to as measured scattering spectrum, scattered by the object at a scattering angle θ comprised between 1° and 15°; these detection means comprising a spectrometric detector;
- computer processing means comprising
- means for determining at least a first characteristic of the object based on the measured transmission spectrum,
- means for verifying the meeting of at least one suspicion criterion concerning the first characteristic determined previously for the object and expressing the fact that the object contains a potentially suspicious material for an application considered, by comparison of the first characteristic as previously determined for the object with a predefined range of values around materials searched for having regard to the application concerned;
- means for determining a second characteristic of the object, based on either the measured scattering spectrum, or both on the measured scattering spectrum and on the measured transmission spectrum, and means for comparing with characteristics of calibration materials stored in a database, either of the second characteristic, or of the first and second characteristics, for the purposes of identification of a material constituting the object.

According to a first possible embodiment, the detection means comprise, in addition to the spectrometric detector defined previously, positioning means for the successive positioning of said spectrometric detector in a position for transmission for acquiring the measured transmission spectrum, and in a position for scattering for acquiring the measured scattering spectrum. According to a second possible embodiment, the detection means comprise, in addition to the spectrometric detector defined previously, which is then placed for scattering, another spectrometric detector, placed for transmission.

The detection system according to the invention further comprises, preferably, one or more of the following features:
- the first characteristic is chosen from a shape the object, a dimension the object, a thickness of a material constituting the object, a coefficient of attenuation at one or more predetermined energies or over a predetermined range of energies, of a material constituting the object, an effective atomic number $Z_{\textit{eff}}$ of a material constituting the object, an indication as to the nature of a material constituting the object (first estimation of the nature of the material—which is to be confirmed using the scattering spectrum in the second part of the method—or identification of a family or of a type of materials),
- the second characteristic is chosen from a scattering signature representing Bragg peaks or a molecular interference function, of the momentum transfers.
- The computer processing means are configured to implement a method based on an inverse problem type approach and to estimate an overall response matrix of the detection system.

The computer processing means are configured to estimate an incident spectrum attenuated by the object using the measured transmission spectrum.

The computer processing means are configured to construct an overall response matrix of the detection system, from an estimated attenuated incident spectrum, from a calibrated angular response matrix of the detection system as well as, possibly, from a calibrated response matrix of the spectrometric detector placed for scattering and possibly from a calibrated response matrix of the spectrometric detector placed for transmission.

The radiation source is polychromatic.

The radiation source is a source of X-rays.

The spectrometric detector placed for scattering is configured so as to present a detection axis forming, with a central axis of the incident radiation, a scattering angle θ comprised between 1° and 10° and preferably between 1° and 5°.

The detection system comprises a first collimator, referred to as source collimator, placed between the photon radiation source and the object receiving zone, so as to collimate the radiation emitted by the source into an incident beam of central axis Z, The detection system comprises a second collimator, referred to as scattering collimator, between the object receiving zone and the spectrometric detector placed for scattering, the scattering collimator having a central collimation axis forming a scattering angle θ with the incident central axis Z, which scattering angle θ is preferably comprised between 1° and 5°.

The spectrometric detector or detectors used contain direct conversion sensors, i.e. the X photons incident on the sensor are absorbed by a semiconductor (CdTe for example) and create a cloud of electron charges (typically 10000 electrons for one X photon of 60 keV). These charges are then collected by electrodes and form a transient electrical signal called a pulse. If the collection is complete, the integral of the measured pulse for each detected particle is proportional to its energy deposited in the semiconductor. An electronic circuit makes it possible to measure this integral. After digitization, the different measurements of photons of the same energy are summed, which makes it possible to reconstruct the spectrum of the X-rays that interacted with the irradiated object.

The invention covers a detection system and a method of analyzing an object which are characterized in combination by all or some of the features mentioned above and below.

BRIEF DESCRIPTION OF THE DRAWING

Other details and advantages of the present invention will appear from the reading of the following description, which refers to the diagrammatic appended drawings and which relates to preferred embodiments, provided by way of non-limiting examples. In the drawings.

DETAILED DESCRIPTION

Figure 3:
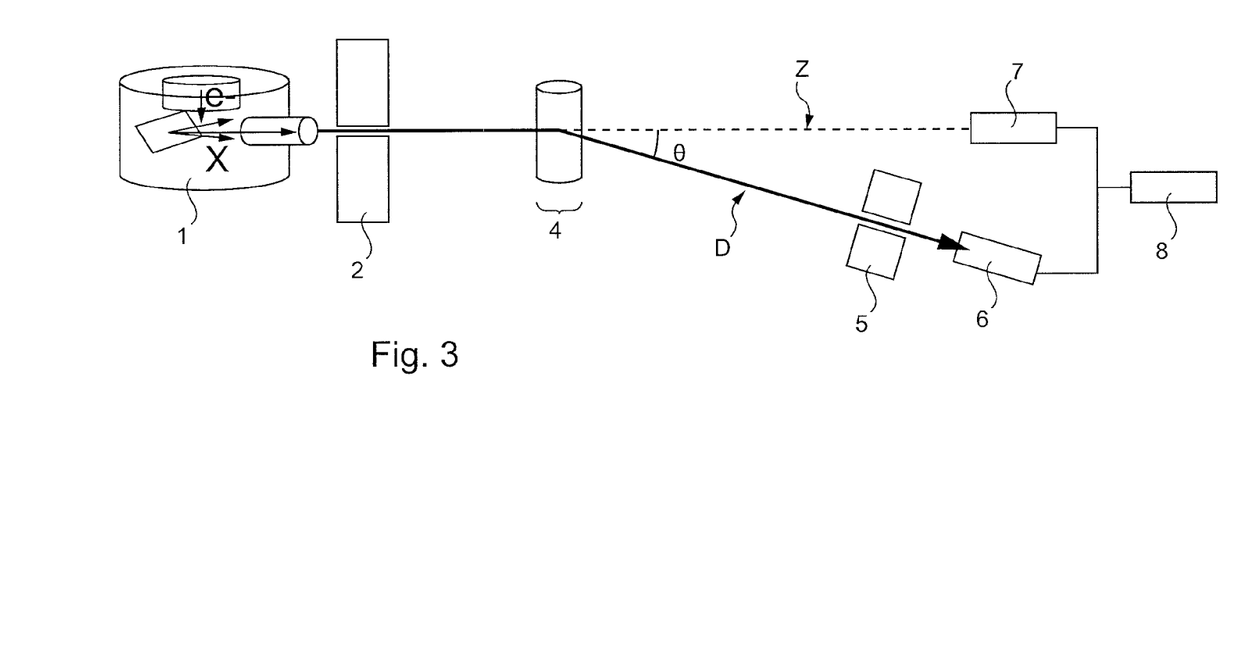
FIG. 3 is a diagrammatic view of a detection system according to the invention.

The detection system according to the invention illustrated in FIG. 3 comprises:
- a polychromatic source 1 of ionizing radiation, such as an X-ray tube,
- a source collimator 2, which makes it possible to channel the radiation from source 1 into an incident beam of central axis Z,
- a receiving zone 4 for an object to analyze;
- a scattering collimator 5 having a collimation axis D,
- a spectrometric detector 6 placed for scattering, which is associated with the scattering collimator 5 such that the detector 6 detects a radiation scattered at a scattering angle θ (angle between the incident axis Z and the axis of collimation and detection D) for example equal to 2.5 (the representation in FIG. 3 not being to scale); the spectrometric detector 6 placed for scattering is configured to establish a measured scattering spectrum (of energy), that is to say an energy spectrum of the radiation scattered by the object in the direction D; the spectrometric detector 6 is, in the example, a semiconductor material detector, such as a detector with CdTe or CdZnTe;

a spectrometric detector 7 placed for transmission, configured to establish a measured transmission spectrum (of energy), that is to say an energy spectrum of the radiation transmitted by the object in the direction Z; the spectrometric detector 7 placed for transmission is, in the example, a semiconductor material detector, such as a detector with CdTe or CdZnTe;

computer processing means 8 for processing measured spectra supplied by the spectrometric detectors 6 and 7.

The terms "transmitted radiation" designate the radiation constituted by photons which have undergone no interaction in the examined object. By "transmission spectrum" is meant the radiation spectrum transmitted along the axis of the incident beam to the object, constituted by the photons which have undergone no interaction in the object. The expression "placed for transmission" designates a detector configured to detect the radiation transmitted by the material. Thus, a detector placed for transmission is situated on the axis of the radiation that is incident to the object, the object being placed between the detector and the radiation source.

By "spectrometric detector" is meant a detector configured to generate an energy spectrum of the detected radiation.

The method according to the invention is directed to determining whether or not an object to analyze is dangerous (explosive, tumor, etc.). For this, the method takes place in two parts. The objective of the first part of the method is not the precise identification of the material constituting the object; this first part is only directed to determining whether the object is suspicious or not, that is to say to determine whether the object merits a more thorough analysis being carried out. This first part thus enables the analysis to be shortened for a high number of objects which clearly prove to be inoffensive.

The method described here has been implemented by the inventors to study two cylindrical samples of 40 mm diameter constituted respectively by acetone ($C_2H_6CO$) and water ($H_2O$).

For each inspected sample, the first part of the method exploits a measured transmission spectrum as supplied by the spectrometric detector 7, and of which the direct model is the following:

$$h = R_{Et} \cdot (S_{inc} \times Att)$$

With:
h: the vector of the measured transmission spectrum of size ($Nb_{Ejt} \times 1$)

$R_{Et}$: the response matrix of the spectrometric detector placed for transmission, of size ($Nb_{Ejt} \times Nb_{Ei}$). In the case of a perfect detector, this matrix is a diagonal matrix. Each term $R_{Et}(j,i)$ of the matrix represents the probability of detecting an energy value equal to j when the photon which is incident on the detector has an energy i.

$S_{inc}$: the vector of the incident spectrum of the X-ray tube 1 of size ($1 \times Nb_{Ei}$)

Att: the attenuation vector of size ($1 \times Nb_{Ei}$) which takes into account the effects of attenuation in the object.

The vector ($S_{inc} \times Att$) represents the spectrum of the radiation source attenuated by the object. In the example described here, and which supplies very precise signatures, this vector is taken into account in the construction of an overall response matrix A of the system, as will be understood later.

$Nb_{Ejt}$ and $Nb_{Ei}$ respectively correspond to the number of channels of the measured transmission spectrum (that is to say to the number of channels of the energy spectrum detected by the detector placed for transmission) and to the number of channels of the incident energy spectrum.

The symbol x corresponds to a term by term product ($S_{inc}$ and Att are multiplied term by term and a vector is then obtained which has the same size).

The symbol . corresponds to the conventional matrix product.

Figure 4:
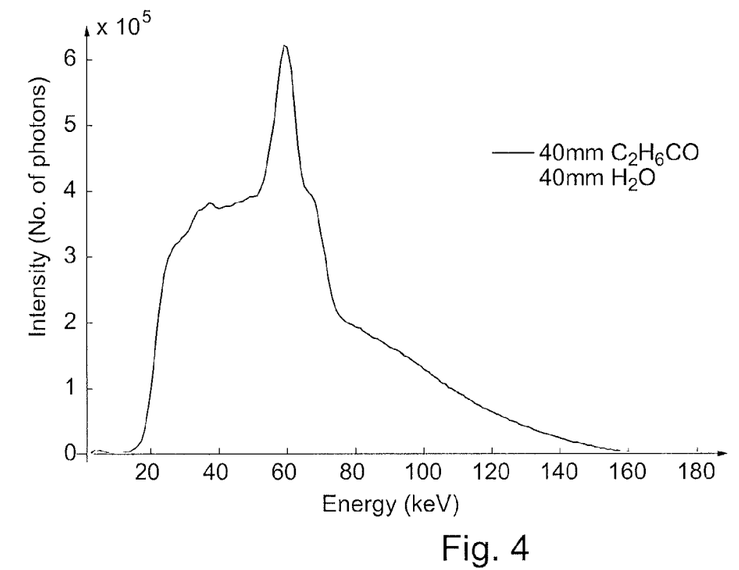
FIG. 4 is a graph representing transmission spectra for cylindrical samples of 40 mm diameter of water ($H_2O$) and acetone ($C_2H_6CO$), as measured by the spectrometric detector placed for transmission of the detection system of FIG. 3.

The transmission spectra measured with the spectrometric detector 7 for the aforementioned samples of acetone ($C_2H_6CO$) and water ($H_2O$) may be observed in FIG. 4.

Several characteristics may be extracted from such a transmission spectrum: attenuation coefficient, effective atomic number $Z_{eff}$ of a material constituting the object, an estimation of the nature, or even of the nature and of the thickness, of a material constituting the object.

The effective atomic number $Z_{eff}$ of the material may for example be obtained by a statistical method which compares the transmission spectrum measured for the object with spectra of calibration samples (calibration materials) measured under the same experimental conditions, and which use a physical model of the spectrum change according to the effective atomic number and the thickness of the material. This technique is described in French patent application No. 1363174 of Alexia Gorecki in the name of CEA, incorporated herein by reference.

The transmission spectrum may also be employed to estimate the nature of the material examined. The estimation of the nature of a material, as well as possibly its thickness, based on a transmission spectrum is described in the applications WO2012000993 or WO2011069748, in the name of the CEA, incorporated herein by reference. Once this characteristic or these characteristics of the object have been estimated, a decision is taken.

If the object inspected appears suspicious, that is to say if one or more suspicion criteria are met (doubtful form, or atomic number belonging to a critical range of values of potentially dangerous materials defined in advance according to the application concerned), then a scattering spectrum of the material will be acquired and studied to enable better discrimination of the material. This second part is not always carried out on all materials since, although highly discriminating, it requires a relatively long time of exposure to the X-rays.

If there is no doubt as to the innocuousness of the object, the first part of the method is conducted on a new object.

The effective atomic number of the two inspected samples (water and acetone) has been evaluated on the basis of the spectra of FIG. 4. The following results were obtained:

for the sample of water: estimated $Z_{eff}$=7.21. In theory, such a sample possesses an effective atomic number: theoretical $Z_{eff}$=7.22. It is thus found that the result obtained is very close to the theoretical value for the sample.

For the sample of acetone: estimated $Z_{eff}$=6.05, for a theoretical atomic number: $Z_{eff}$ theoretical=6.03.

A critical zone has been defined for this application (detection of explosives); it corresponds to materials of which the $Z_{eff}$ is between 6 and 8.5. In other words, the step of verifying the meeting of the suspicion criterion consists of comparing the determined effective atomic number, estimated on the basis of the measured transmission spectrum, with the range of values [6;8.5]. It is to be noted that several discontinuous critical zones (several ranges of values) may be defined for the same first characteristic (for example atomic number).

It is also possible to define several suspicion criteria relating to distinct characteristics; in this case, it may be considered either that the object is suspicious (and thus eligible for the second part of the method) when at least one of these suspicion criteria is met, or that the object is only suspicious if all the suspicion criteria are met.

The two samples inspected here (water and acetone) have $Z_{eff}$ that are in the critical zone; they are thus considered as suspicious and the second part of the method according to the invention, i.e. the study of these two samples for small angle scattering, must therefore be executed.

The second part of the method is directed to precisely identifying the material constituting the object when it has been considered as suspicious further to the first part. This second part consists for example of providing a scattering signature of said material on the basis of a measured scattering spectrum (provided by the spectrometric detector 6), the terms "scattering signature" designating a function representative of the material and showing scattering peaks (Bragg peaks or Molecular Interference Function according to the nature—crystalline or amorphous—of the material).

Figure 5:
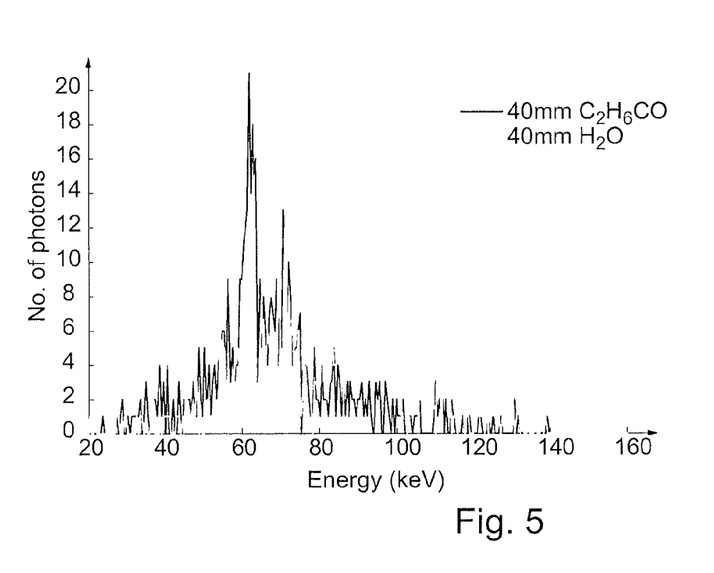
FIG. 5 is a graph representing scattering spectra for cylindrical samples of 40 mm diameter of water ($H_2O$) and acetone ($C_2H_6CO$), as measured by the spectrometric detector placed for scattering of the detection system of FIG. 3.

The scattering spectra measured by the detector 6 for the two samples may be observed in FIG. 5. In the example described here, it has been chosen to exploit, in an original way, the measured scattering spectra in combination with the measured transmission spectra in the course of the first part of the method. As a variant, it is possible to exploit the measured scattering spectra of FIG. 5 according to another technique such as a known technique used in EDXRD.

In the example chosen here, the second part of the method uses the following model, describing the relationship between the scattering signature f of the material and the measured scattering spectrum g:

$$g = (R_{Ed} \times S_{inc} \times Att) \cdot R_\theta \cdot f = A \cdot f$$

With:
- g: the vector of the measured (coherent) scattering spectrum, of size ($Nb_{Ejd} \times 1$)
- $R_{Ed}$: the response matrix of the spectrometric detector placed for scattering, of size ($Nb_{Ejd} \times Nb_{Ei}$). In the case of a perfect detector, this matrix is a diagonal matrix. Each term $R_{Ed}(j,i)$ of the matrix represents the probability of detecting an energy value equal to j knowing that the radiation which is incident on the detector has an energy equal to i. In general, the response matrix of a spectrometric detector establishes a probabilistic relationship between an energy detected by the detector and the energy of the radiation that is incident on that detector. Each column i of $R_{Ed}(j,i)$, with j varying from 1 to $Nb_{Ejd}$, corresponds to the probability density of energy detected by the detector when the latter is subjected to incident radiation of energy i.
- $S_{inc}$: vector of the incident spectrum of the X-ray tube of size ($1 \times Nb_{Ei}$)
- Att: attenuation vector of size ($1 \times Nb_{Ei}$) which takes into account the effects of attenuation in the object. On account of the low value of the age θ, less than 15° and preferably less than 10° or even 5°, the approximation will be made that the attenuation by the object along the path to the two detectors (for scattering and for transmission) is the same.
- $R_\theta$: angular response matrix of the detection system, of size ($Nb_{Ei} \times Nb_x$). Each term $R_\theta(j,k)$ of the matrix $R_\theta$ corresponds to a probability that the energy of a photon detected at the energy j corresponds to a momentum transfer equal to k. In other words, $R_\theta(j, k)$ corresponds to the probability that a momentum transfer k gives rise to the detection of a photon of energy j. Each column k $R_\theta(j,k)$, with j varying from 1 to $Nb_{Ejd}$, corresponds to the probability density of energy detected by the detector when there is a momentum transfer equal to k. More generally, the angular response matrix $R_\theta$ enables a probabilistic relationship to be established between the energy detected by the detector placed for scattering and an elastic scattering parameter of a material constituting the object, in particular the momentum transfer.
- f: scattering signature, of size ($1 \times Nb_x$), specific to the material constituting the object, which makes it possible to describe either the theoretical Bragg peaks of the material in the case of a crystalline material, or the molecular interference function in the case of an amorphous material,
- A: overall response matrix of the system for scattering, of size ($Nb_{Ejd} \times Nb_x$). Each term $A(j,k)$ of A corresponds to a probability that the energy of a photon detected, by the detector for scattering, at the energy j corresponds to a momentum transfer equal to k. In other words, $A(j,k)$ corresponds to the probability that a momentum transfer k gives rise to the detection of a photon at the energy j.

The symbol x corresponds to the term by term product ($S_{inc}$ and Att are multiplied term by term and a vector is then obtained which has the same size).

The symbol . corresponds to the conventional matrix product.

$Nb_{Ejd}$, $Nb_{Ei}$ and $Nb_x$ respectively correspond to the number of channels of the measured scattering spectrum (that is to say to the number of channels of the energy spectrum detected by the detector placed for scattering), to the number of channels of the spectrum of the incident energy and to the number of channels of the vector describing the momentum transfer.

It is to be noted that the number of photons detected in each channel of the vector g follows a Poisson distribution having as parameter the average number of photons in that channel.

The method according to the invention then comprises an operation of constructing an overall response matrix A of the detection system, using the above model. For this, the terms $R_\theta$ and ($S_{inc} \times Att$), and possibly $R_{Ed}$ should be determined in advance.

Each of these steps is individually described later.

The prior step of calibrating the response matrix $R_{Ed}$ of the spectrometric detector placed for scattering is not necessary but advantageous, since it takes into account the degradation of the spectra due to the response of the detector. However, this step is optional or even unnecessary, in particular for detectors that are sufficiently energy resolving and when the response of a detector is judged to be satisfactory. The same applies for the response matrix $R_{Et}$ of the spectrometric detector placed for transmission, use later.

Once the overall response matrix A has been constructed using the aforementioned model, the method according to the invention reconstructs the signature f (molecular interface function for amorphous materials, distribution of the $d_{hkl}$ for the polycrystalline materials) based on the model g=A·f (where A and g are then known) by implementing a method based on an inverse problem type approach.

The Maximum Likelihood—Expectation Maximization algorithm (denoted MLEM) is available to estimate the spectrum to be calculated by iterative maximization of the function of log-likelihood. This type of calculation is very frequent when it is required to estimate a maximum likelihood, and relies on a more general algorithm, called Expectation—Maximization (EM). This method has the advantage of taking into account the Poisson-like nature of the measured data.

The coefficients of the overall response matrix A of the system are denoted $a_{i,j}$. It is wished to maximize the probability that the estimated f of dimension $Nb_x$ generates measurements g. It is furthermore known that the measured data follow a Poisson distribution, on account of their physical nature. The likelihood function of the estimated f can thus be written:

$$Pr(g/f) = \prod_{j=1}^{Nb_{Ejd}} \frac{e^{-\sum_{k'=1}^{Nbx} a_{j,k} f_k} \left(\sum_{k=1}^{Nbx} a_{j,k} f_k\right)^{g_j}}{g_j}$$

Its log-likelihood is then expressed $$\Phi(f) = \log Pr(g/f) = \sum_{j=1}^{Nb_{Ejd}} \left(-\sum_{k=1}^{Nbx} a_{j,k} f_k + g_j \log\left(\sum_{k=1}^{Nbx} a_{j,k} f_k\right)\right)$$

Next it is sought to maximize this function, by cancelling its derivative:

$$f_k \frac{\partial \phi(f)}{\partial f_k} = 0$$

The iterative solution of this problem is then written:

$$f_k^{n+1} = f_k^n \frac{1}{\sum_{j=1}^{Nb_{Ejd}} a_{j,k}} \sum_{j=1}^{Nb_{Ejd}} \left(\frac{g_j a_{j,k}}{\sum_{k'=1}^{Nbx} a_{j,k'} f_{k'}^n}\right)$$

By initializing the vector $f^{(0)}_k$ with positive values, it is ensured to have non-negative results.

Figure 6:
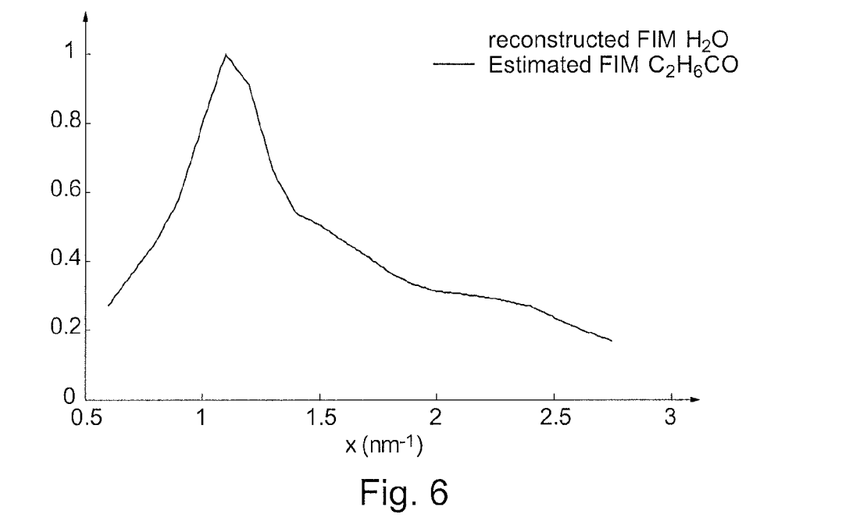
FIG. 6 is a graph representing the scattering signature (estimated MIF) of a cylindrical sample of water of 40 mm diameter and that of a cylindrical sample of acetone of 40 mm diameter, as reconstructed on the basis of a method and a detection system according to the invention.

Thus, based on an estimation of A and of the measurement of g, it is possible to reconstruct f by iterating the MLEM algorithm. The results of this reconstruction (denoted "reconstructed FIM" in FIG. 6) for the samples of water and acetone inspected, by employing a MLEM algorithm with 100 iterations, are illustrated in FIG. 6.

In other words, based on measurements carried out for transmission and for scattering on an unknown object, a function can be reconstructed relative to the structure of a material constituting that object. The values of this function are represented in the matrix A.

As this material is unknown, the objective is to identify it. For this, a set of calibration materials is used (of explosive and non-explosive type in the case of an application for analyzing baggage for example; of healthy and tumorous biological tissue type in the case of a medical analysis application) of which the effective atomic numbers or other first characteristic and of which the signatures for scattering (molecular interference function or Bragg peaks) or other second characteristic are tabulated and stored in a database, and the analyzing method according to the invention next consists of comparing the values obtained for the object and of analyzing with those of the database, to identify the unknown object.

As a variant, some parameters making it possible to obtain structural parameters of the material are extracted from the signature reconstructed for the object; for example, in the case of a crystalline material, the extraction of the position of the peaks present in the signature obtained makes it possible to obtain the interplanar spacings of the crystal.

Figure 7:
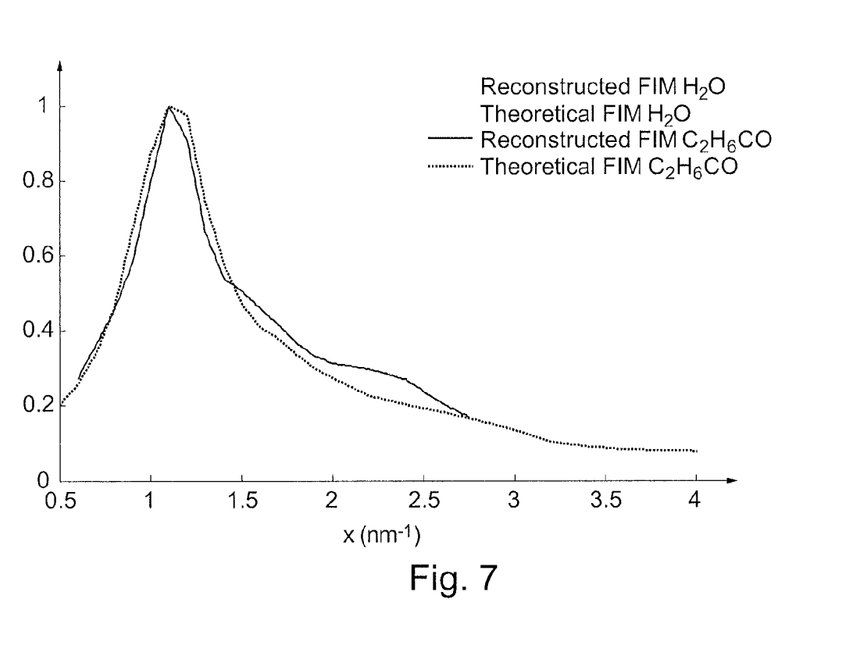
FIG. 7 is a graph representing the scattering signature ("reconstructed MIF") of a cylindrical sample of water of 40 mm diameter and that of a cylindrical sample of acetone of 40 mm diameter, as reconstructed on the basis of a method and a detection system according to the invention, and also representing the theoretical scattering signatures ("theoretical MIF") of these samples.

By comparing the values of estimated $Z_{eff}$ with a base of values of theoretical $Z_{eff}$ for a set of materials and furthermore comparing the form of the reconstructed molecular interference functions with a form base of molecular interference functions for a set of materials, it is possible to identify the nature of the two samples analyzed (water and acetone). FIG. 7 makes it possible to compare the reconstructed molecular interference functions of the two samples analyzed (water and acetone) and their theoretical molecular interference functions.

There are now described the various steps of the operation of constructing the overall response matrix A of the system.

Prior to any analysis of an object, that is to say "off-line", calibration operations are carried out to determine certain specifications of the detection system, which depend in particular on the detectors used and on the geometry of the system, and which, contrary to the attenuation vectors, do not depend on the object to analyze. These specifications are $R_{Et}$, $R_{Ed}$, $R_\theta$. They are next stored in the computer processing means 8.

The response matrix $R_{Et}$ of the spectrometric detector 7 placed for transmission may be obtained from the Monte-Carlo Tasmania simulation software application, which makes it possible to simulate the whole detection chain of a semiconductor detector (photon interactions, transit of charge carriers, etc.). Preferably, this simulation is furthermore compared together with experimental data acquired for example with gamma sources. This makes it possible to adjust the energy resolution obtained on simulation.

Figure 8:
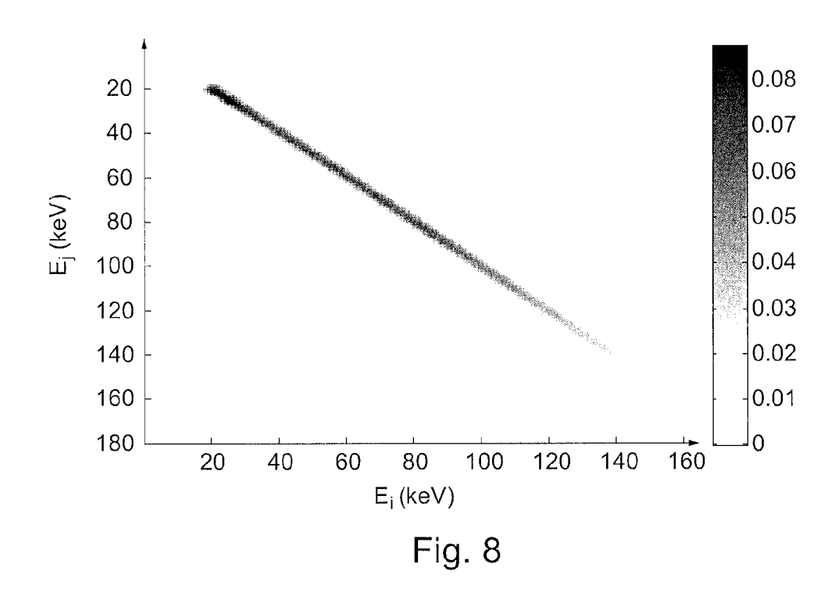
FIG. 8 is a graph representing a response matrix of the spectrometric detector placed for transmission of the detection system of FIG. 3.

FIG. 8 shows the response matrix $R_{Et}$ calibrated for the spectrometric detector 7 placed for transmission. This matrix defines the probability of detecting a photon at the energy Ej when the incident energy of the photon is Ei. This probability is indicated in FIG. 8 by gray tones (of which the scale has been transferred to the right of the graph), the x-axis of the graph representing the incident energy Ei expressed in keV, the y-axis corresponding to the detected energy Ej expressed in keV. In the case of a perfect detector, the matrix is diagonal (if it is square).

In similar manner, a prior operation of calibrating a response matrix $R_{Ed}$ of the spectrometric detector 6 placed for scattering is executed "off-line", by simulation using the Monte-Carlo simulation software application and/or by experiment.

Figure 9:
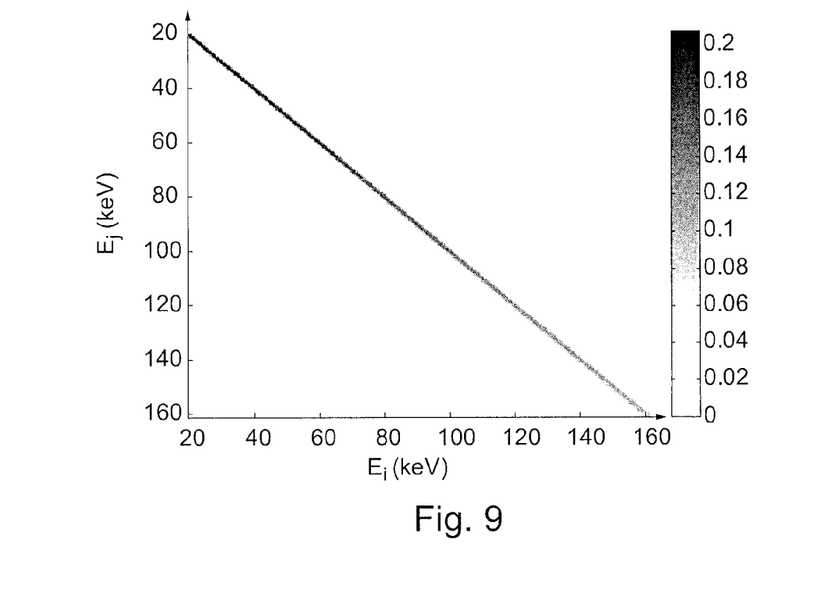
FIG. 9 is a graph representing a response matrix of the spectrometric detector placed for scattering of the detection system of FIG. 3.

The calibrated response matrix $R_{Ed}$ obtained is illustrated in FIG. 9. Here too, the x-axis represents the incident energy Ei in keV, and the y-axis corresponds to the detected energy Ej in keV, the probability of the pair (Ei, Ej) being expressed by gray tones.

A prior operation of calibrating an angular response matrix $R_\theta$ of the detection system is also executed "off-line". This angular response depends on two factors. The first corresponds to the geometry of the acquisition system and more specifically to the opening of the source collimator 2 and to the opening of the scattering collimator 5, knowing that it is assumed that the object fills the intersection of two cones, i.e. an irradiation cone and an observation cone. The irradiation cone delimits the solid angle under which the object sees the source, whereas the observation cone corresponds to the solid angle under which the detector sees the object. First of all an angular distribution 1D of the system is evaluated, either based on simulations, or based on calibrations. Using the relationship linking x (momentum transfer), E (energy that is incident on the detector placed for scattering) and θ (scattering angle), there is deduced the matrix of angular response function of Ei (incident Energy) and of x based on the angular distribution 1D function of θ.

Figure 10:
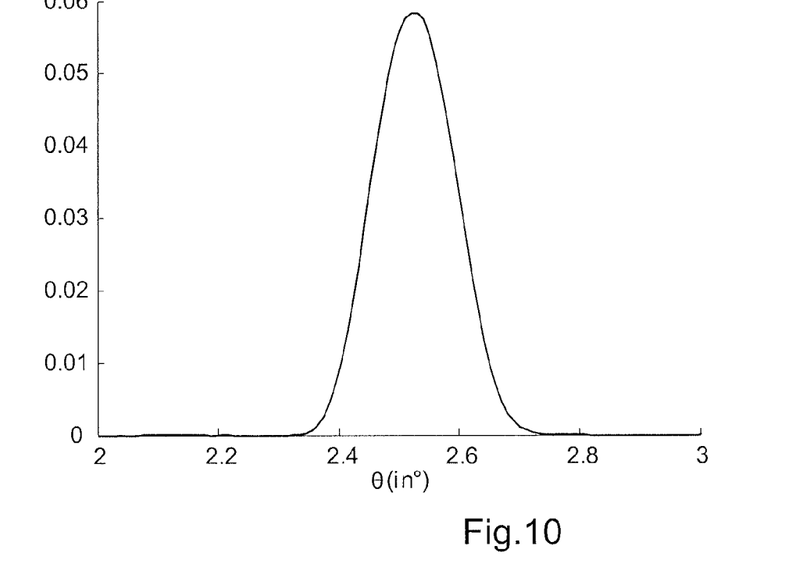
FIG. 10 is a graph representing the angular distribution of the spectrometric detector placed for scattering of the detection system of FIG. 3.
Figure 11:
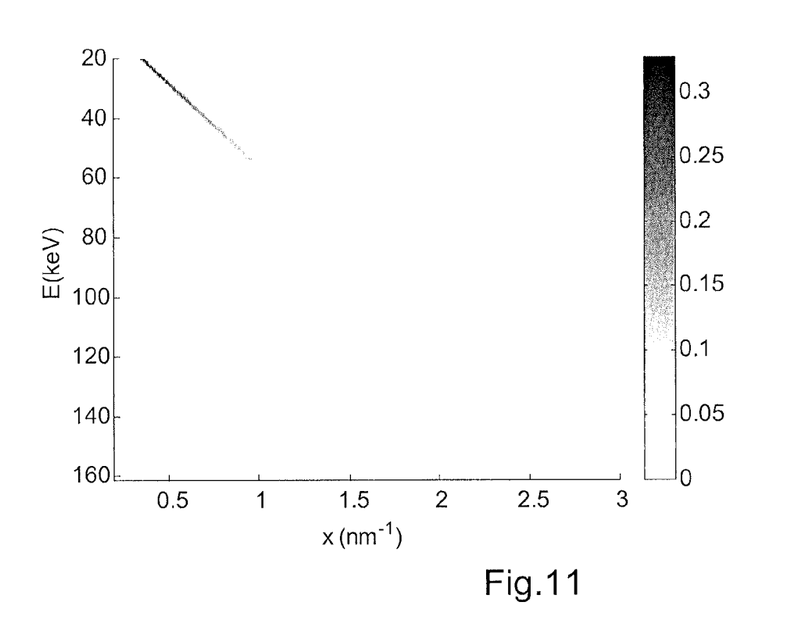
FIG. 11 is a graph representing an angular response matrix of the detection system of FIG. 3.

FIG. 10 shows an example of angular distribution 1D of the scattering system when the collimation axis D of the scattering collimator defines a scattering angle θ equal to 2.5°, the angular distribution expressing the relative quantity of photons that are incident on the detector placed for scattering (y-axis) according to the detection angle in degree (x-axis). This is an example since the use of collimators having different configurations (in particular width and length of the opening of the collimators) would lead to another graph being obtained. An angular response matrix $R_\theta$ of the detection system may be observed in FIG. 11, of which the x-axis represents the momentum transfer x in $nm^{-1}$, while the y-axis represents the energy E that is incident on the detector placed for scattering in keV, the gray tones expressing the relative quantity of incident photons. As referred to previously, this matrix defines a probabilistic relationship between the number of photons incident on the detector placed for scattering, at a given energy, and the momentum transfer.

The construction of the overall response matrix A of the detection system using the model $A=(R_{Ed} \times S_{inc} \times Att) \cdot R_\theta$ still requires a step of estimating an incident spectrum attenuated by the object ($S_{inc} \times Att$).

Advantageously, this step of estimating the attenuated incident spectrum again uses the transmission spectrum measured in the first part of the method by the spectrometric detector 7 placed for transmission. This transmission spectrum h may be written:

$$h = R_{Et} \cdot (S_{inc} \times Att)$$

In other words, it is considered in this version of the invention that the term ($S_{inc} \times Att$) in the expression of the matrix A is equal to the term ($S_{inc} \times Att$) in the expression of the transmission spectrum h. The inventors have shown that this approximation is entirely acceptable for scattering at small angles (less than 15°) and that it enables signatures f to be obtained of an excellent resolution and accuracy for scattering angles less than 5°.

To estimate ($S_{inc} \times Att$) based on the measured transmission spectrum h and on the calibrated response matrix $R_{Et}$ of the detector, the system according to the invention advantageously again uses a technique of MLEM type.

Figure 12:
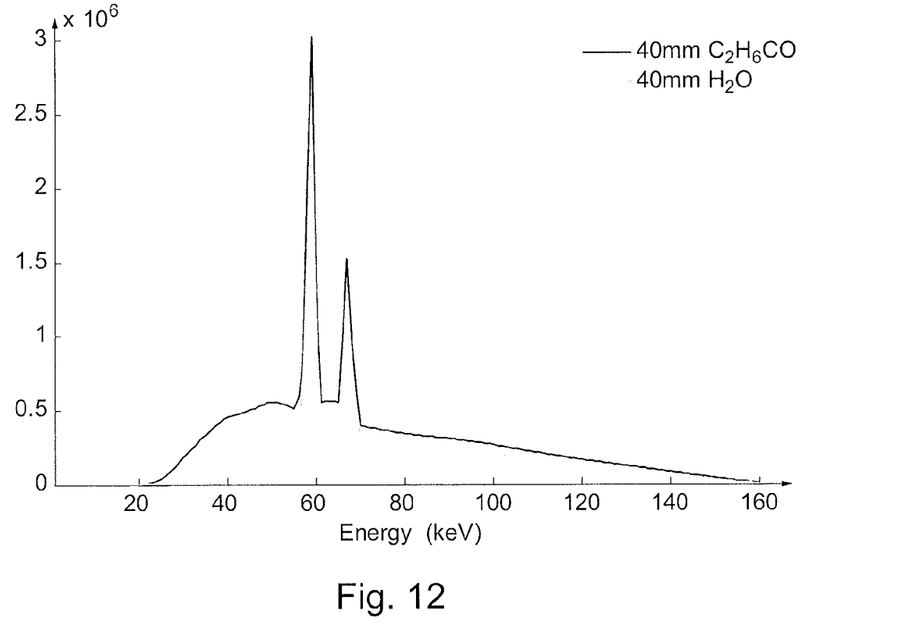
FIG. 12 is a graph representing estimated attenuated incident spectra for cylindrical samples of 40 mm diameter of acetone and water, as estimated according to the invention from measured transmission spectra of FIG. 4.

FIG. 12 shows the different spectra ($S_{inc} \times Att$) obtained after MLEM inversion of the experimental data recorded on the spectrometric detector 7 placed for transmission for the two inspected samples (water and acetone), which data (measured transmission spectra) are illustrated in FIG. 4.

Figure 13:
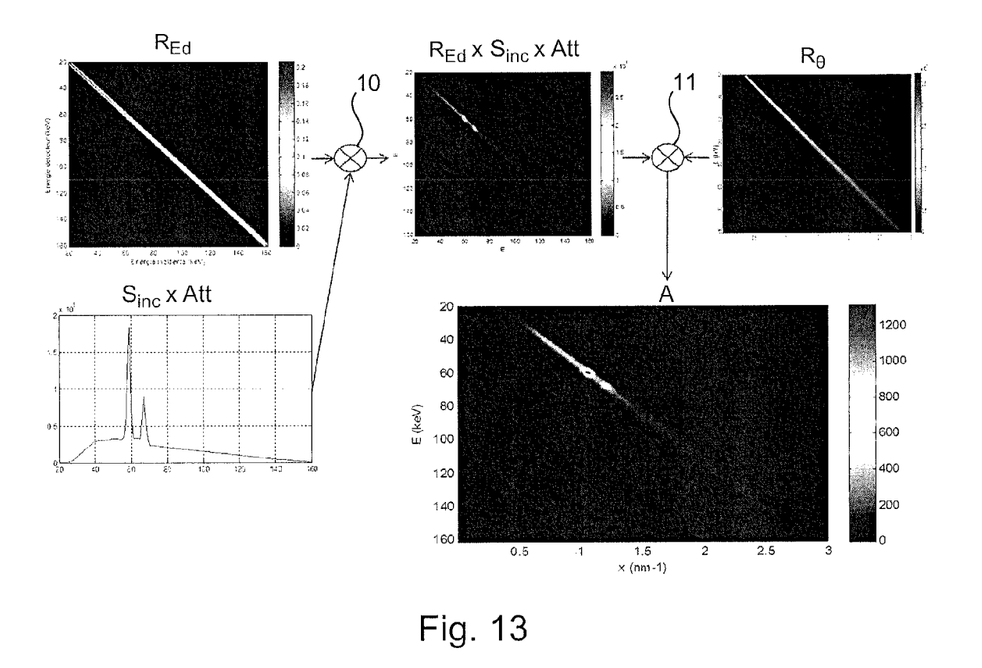
FIG. 13 is a diagram illustrating an operation of reconstruction of an overall response matrix of the detection system of FIG. 3.
Figure 14:
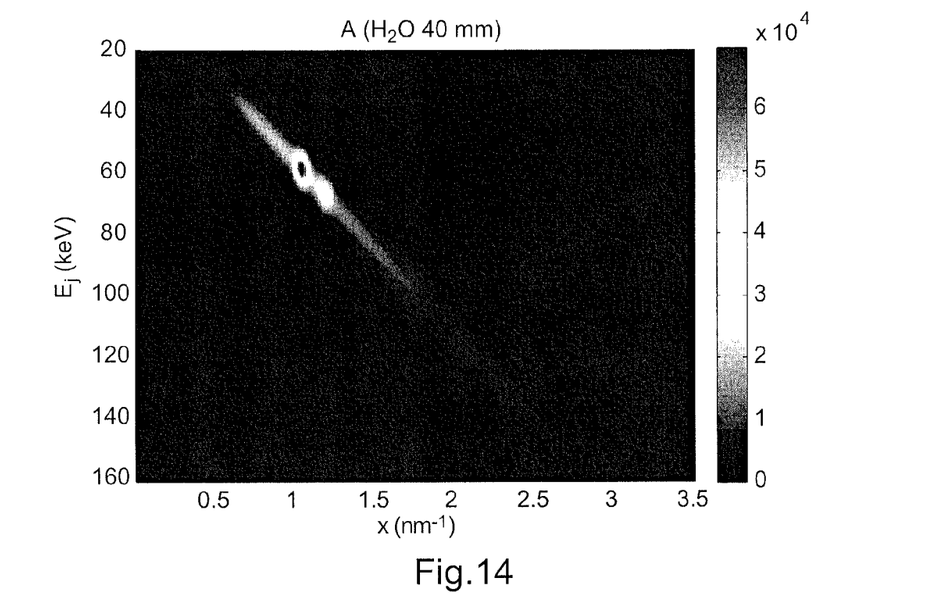
FIG. 14 is a graph representing the overall response matrix A of the detection system of FIG. 3 for a cylindrical sample of water of 40 mm diameter.
Figure 15:
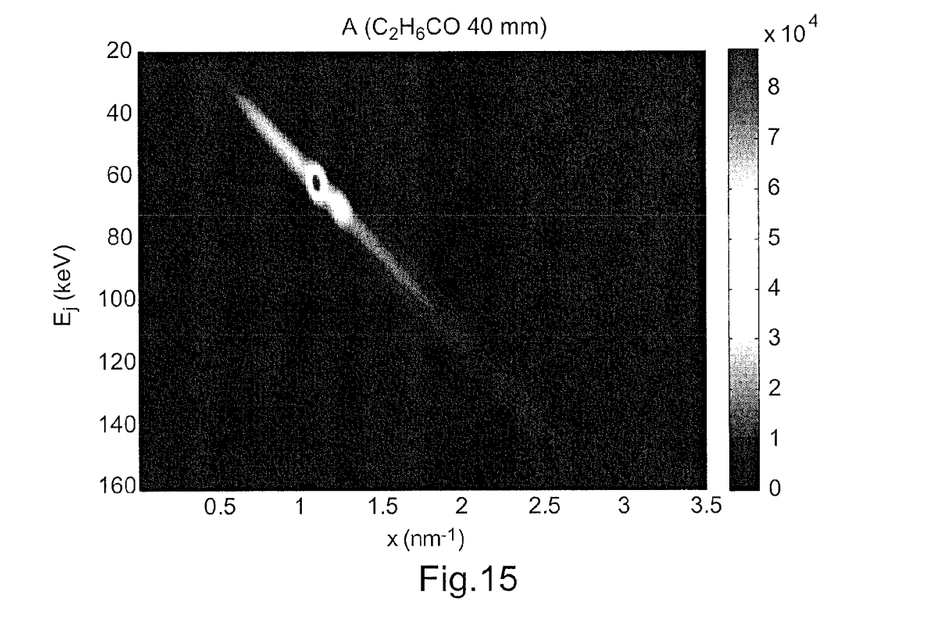
FIG. 15 is a graph representing the overall response matrix A of the detection system of FIG. 3 for a cylindrical sample of acetone of 40 mm diameter.

All the terms of the overall response matrix A of the system have been calibrated, the method according to the invention taken as example next consists of combining them according to the formula $A=(R_{Ed} \times S_{inc} \times Att) \cdot R_\theta$. This combination is summarized in FIG. 13 in which the numerical reference 10 designates a row by row multiplication and in which the numerical reference 11 designates a matrix multiplication. The overall response matrices A obtained may be observed in FIG. 14 for the sample of water and in FIG. 15 for the sample of acetone.

The invention may be the subject of numerous variants in relation to the preferred embodiment described above. Thus for example, the second part of method may consist of a conventional analysis by diffractometry using the EDXRD technique for example. Furthermore, the detector placed for transmission may be a simple integration detector, in which case the first characteristic of the object evaluated for the purposes of verifying a suspicion criterion is not the effective atomic number of the material.

The invention claimed is:

1. A method for analyzing an object in the context of a given application, comprising two parts, a first part comprising:

irradiating the object with incident photon radiation;

acquiring a measured transmission spectrum of energy transmitted by the object using a spectrometric detector placed for transmission;

determining at least a first characteristic of the object based on the measured transmission spectrum;

verifying the meeting of at least one suspicion criterion, the suspicion criterion comprising at least one predefined range of values of the first characteristic corresponding to materials searched for having regard to the given application, the verification of the suspicion criterion comprising a step of comparing the first characteristic as determined previously for the object with the predefined range of values, and a second part executed only when the suspicion criterion is met, the second part comprising:

acquiring a measured scattering energy spectrum scattered by the object at a scattering angle (θ) comprising between 1° and 15° using a spectrometric detector placed for scattering;

determining a second characteristic of the object from either the measured scattering spectrum, or both the measured scattering spectrum and the measured transmission spectrum, and comparing either the second characteristic of the object, or both the first and second characteristics of the object, with characteristics of calibration materials stored in a database, for the purposes of identifying a material constituting the object.

2. The analyzing method according to claim 1, wherein the first characteristic is selected from a form, a dimension, a coefficient of attenuation for one or more predetermined energies or for a predetermined range of energies, an indication as to the nature of a material constituting the object, or an effective atomic number.

3. The analyzing method according to claim 1, wherein the second characteristic is selected from a momentum transfer or a scattering signature representative of the object and showing scattering peaks, reconstructed from both the measured scattering spectrum and the measured transmission spectrum.

4. The analyzing method according to claim 3, wherein the reconstruction of the scattering signature of the object comprises an operation of constructing an overall response matrix (A) of the detection system, which overall response matrix (A) establishes a relationship between an energy detected by the detector placed for scattering and a momentum transfer in the object.

5. The analyzing method according to claim 4, wherein the operation of constructing the overall response matrix (A) of the detection system is made on the basis of an estimated attenuated incident spectrum (Sinc×Att) and of a calibrated angular response matrix ($R_\theta$) of the detection system.

6. The analyzing method according to claim 5, wherein the operation of constructing the overall response matrix (A) of the detection system is further made on the basis of a response matrix ($R_{Ed}$) of the spectrometric detector placed for scattering and of a response matrix ($R_{Et}$) of the spectrometric detector placed for transmission.

7. A detection system for analyzing an object in the context of a given application, the system comprising:
- a source of photon radiation;
- a zone for the reception of an object to analyze;
- a spectrometric detector, downstream of the object receiving zone, for acquiring an measured transmission energy spectrum transmitted by the object and for acquiring a measured scattering spectrum scattered by the object at a scattering angle θ comprising between 1° and 15°;
- a computer processing means configured to analyze the measured transmission energy spectrum and the measured scattering spectrum and comprising:
  - a means for determining at least a first characteristic of the object based on the measured transmission spectrum;
  - a means for verifying the meeting of at least one suspicion criterion concerning the first characteristic of the object, the verifying means being configured to perform a comparison of the first characteristic as previously determined for the object with a predefined range of values of the first characteristic corresponding to materials searched for having regard to the given application;
  - a means for determining a second characteristic of the object based either on the measured scattering spectrum, or both on the measured scattering spectrum and on the measured transmission spectrum; and
  - a means for comparing with characteristics of calibration materials stored in a database, either for the second characteristic the object, or for the first and second characteristics of the object, for the purposes of identifying a material constituting the object.

8. The detection system according to claim 7, wherein the spectrometric detector is placed for scattering and the detection means further comprises a second spectrometric detector, placed for transmission.

9. The detection system according to claim 7, wherein the spectrometric detector further comprises positioning means for the successive positioning of the spectrometric detector in a position for transmission, for acquiring the measured transmission spectrum, and in a position for scattering for acquiring the measured scattering spectrum.

10. The detection system according to claim 7, wherein the first characteristic is selected from a form, a dimension, a coefficient of attenuation for one or more energies or for a predetermined range of energies, an indication as to the nature of a material constituting the object, or an effective atomic number, and
the second characteristic is selected from a momentum transfer or a scattering signature representative of the object and showing scattering peaks, reconstructed from both the measured scattering spectrum and the measured transmission spectrum.

11. The detection system according to claim 7, wherein the computer processing means are configured to to construct an overall response matrix (A) of the detection system that establishes a relationship between an energy detected by the detector placed for scattering and a momentum transfer in the object, the overall response matrix (A) being constructed from an attenuated incident spectrum (Sinc×Att) estimated using the measured transmission spectrum, and from a calibrated angular response matrix ($R_\theta$) of the detection system.

12. The detection system according to claim 7, wherein the spectrometric detector placed for scattering is configured so as to present a detection axis (D) forming, with a central axis (Z) of the incident radiation, a scattering angle θ comprising between 1° and 5°.

* * * * *